(12) United States Patent
Lang

(10) Patent No.: US 6,743,223 B1
(45) Date of Patent: Jun. 1, 2004

(54) NEUTRAL ELECTRODE

(75) Inventor: Burrhus Lang, Innsbruck (AT)

(73) Assignee: Leonhard Lang KG, Innsbruck (AT)

( * ) Notice: Subject to any disclaimer, the term of this patent is extended or adjusted under 35 U.S.C. 154(b) by 0 days.

(21) Appl. No.: 10/031,802

(22) PCT Filed: Apr. 19, 2000

(86) PCT No.: PCT/AT00/00097
§ 371 (c)(1),
(2), (4) Date: Jun. 24, 2002

(87) PCT Pub. No.: WO00/65992
PCT Pub. Date: Nov. 9, 2000

(30) Foreign Application Priority Data

Apr. 29, 1999 (AT) .............................................. 770/99

(51) Int. Cl.$^7$ .............................................. A61B 18/18
(52) U.S. Cl. .......................... 606/32; 600/372; 600/392
(58) Field of Search ............................... 606/32–35, 41; 600/372–374, 391, 392, 395; 29/825, 829, 885

(56) References Cited

U.S. PATENT DOCUMENTS

| | | | | |
|---|---|---|---|---|
| 4,303,073 A | * | 12/1981 | Archibald | 606/35 |
| 4,694,835 A | * | 9/1987 | Strand | 600/385 |
| 4,699,679 A | * | 10/1987 | Cartmell et al. | 156/242 |
| 4,842,577 A | * | 6/1989 | Konno et al. | 604/20 |
| 4,895,169 A | * | 1/1990 | Heath | 607/142 |
| 5,269,810 A | * | 12/1993 | Hull et al. | 607/129 |
| 5,505,200 A | * | 4/1996 | Takaki | 600/395 |
| 5,520,683 A | | 5/1996 | Subramaniam et al. | 606/32 |
| 5,713,128 A | * | 2/1998 | Schrenk et al. | 29/885 |
| 5,984,102 A | * | 11/1999 | Tay | 206/701 |
| 6,419,798 B1 | * | 7/2002 | Topolkaraev et al. | 204/157.15 |

FOREIGN PATENT DOCUMENTS

| | | |
|---|---|---|
| EP | 0 509 710 A2 | 4/1992 |
| WO | WO 93/00857 | 1/1993 |
| WO | WO 96/32057 | 10/1996 |
| WO | WO 97/24156 | 7/1997 |

* cited by examiner

*Primary Examiner*—Michael Peffley
(74) *Attorney, Agent, or Firm*—Lorusso Loud & Kelly LLP

(57) ABSTRACT

The invention relates to a method for producing medical electrodes, in particular, neutral electrodes. According to the inventive method, a web-shaped laminate, consisting of a non-conductive intermediate support (C) and a conductive layer (A) is coated on the side of said conductive layer with an electrically conductive, adhesive gel (E). The laminate-gel combination is formed to a specific contour, preferably punched out, before being fixed to a carrier (H) by the side opposite to the gel (E). The conductive layer is applied to the web-shaped intermediate support (C) during the production of the laminate, preferably having been previously punched out, as panels which do not cover the entire web-shaped intermediate support (C). The contour forming of the laminate-gel combination, which takes place preferably in a punching-out process is performed in such a way that the gel (E) protrudes over the outer edges of the conductive layer panels which have been pre-formed in the laminate, at least in some areas and preferably on all sides.

17 Claims, 5 Drawing Sheets

NEUTRAL ELECTRODE

BACKGROUND OF THE INVENTION

The invention concerns a process for producing medical electrodes, in particular neutral electrodes, wherein a laminate in web form comprising a non-conductive intermediate carrier and a conductor layer is coated on the side of the conductor layer with an electrically conductive adhesive gel and the laminate-gel combination is shaped to a contour, preferably stamped out, before it is fixed on a carrier on the side remote from the gel. The invention further concerns such a medical electrode.

Medical electrodes are stuck to the skin of a patient for the most widely varying purposes, in order to pick up electrical signals or to introduce and carry away currents (defibrillation neutral electrodes). Particularly in the case of medical bioelectrodes which are used as neutral electrodes in order to carry away currents, it is important that skin contact takes place as uniformly as possible in order to avoid local high current densities. Multi-layer neutral electrodes are already known, which have a carrier for example of foam material on the side which faces away from the skin. The next layer is a laminate comprising an intermediate carrier with a conductor layer, for example aluminum. That conductor layer is then covered on the skin side with an electrically conductive, adhesive gel (for example a skin-friendly hydrogel). In that respect care is to be taken to ensure that the metal conductor layer does not come into direct contact with the skin of the patient.

It is known for the edge of the conductor layer to be covered with gel or an additional insulating element. That structure however is costly and complicated.

In order to shape a covering insulating element, it is necessary to use material of approximately the same surface area as that of the entire electrode, in which case the predominant proportion is cuttings and thus waste.

If the conductor surface is overlappingly covered with gel, that is done using one of two known processes. On the one hand, a flat web of gel can be produced, stamped out in the shape required for the overlapping, and fixed by adhesive precisely over the conductor surface. That process is highly expensive in terms of the material used as additional cover webs have to be employed in the course of the process and it makes high demands in terms of manipulation of the adhesive gel surface.

On the other hand, a liquid pre-mix for the gel can be poured into a reservoir which is provided for that purpose and which is formed by the carrier of the electrode together with the conducting surface (or a cover) and a peripherally extending edge element. That pre-mix then polymerizes, for example with a supply of energy, to form an adhesive hydrogel. In this case also, a considerable amount of waste is produced, for forming the peripherally extending edge element, and handling of the liquid pre-mix is extremely demanding and liable to error. Because of this, such processes are only used by a few manufacturers (possibly only just, one).

SUMMARY OF THE INVENTION

The object of the invention is to provide a process with which it is possible to produce a medical electrode in an automated manufacturing procedure, which involves a uniform and reliable transmission of current between the skin of the patient and the electrode.

A further object of the invention is to provide such an electrode.

The process according to the invention is characterised in that the conductor layer is already applied in manufacture of the laminate to the intermediate carrier in web form—preferably by preceding stamping-out-in the form of fields which do not cover the entire intermediate carrier in web form, and that the operation of shaping the laminate-gel combination to contour—which is preferably effected by stamping out—is effected in such a way that the gel laterally projects at least in a region-wise manner with respect to the outer edges of the conductor layer fields which are preformed in the laminate.

The basic idea of the process of the invention is firstly that manufacture of the electrode does not as usual involve using a laminate in web form, with simply laminating onto a non-conductive intermediate carrier in web form a conductor layer in web form of the same size, but rather providing upon manufacture a special laminate in which substantially discrete individual fields or areas are arranged on the non-conductive intermediate layer. In that way, after the conductive gel has been applied in a further stamping process, it is possible to implement a stamping operation which involves substantially at all sides a lateral spacing in relation to the electrically conductive individual fields. In contrast to the state of the art in which the gel together with the conductor layer was jointly stamped, the process according to the invention now provides that the gel laterally covers over the outer edges of the conductor layer fields which are preformed in the laminate. In that way it is possible to manufacture an electrode in which the conductive adhesive gel layer completely overlaps the conductive (metal) foil wherever contact with the body occurs. That therefore avoids high local current strengths by direct contact of the conductor with the skin, which for example can result in burns. It will be appreciated that the tabs required for connection to the electrode cable can also be caused to project freely without a gel covering in the electrodes according to the invention.

The proposed process is much simpler in procedure than the state of the art as gel coating over the full area involved can be effected. It makes much greater savings in terms of material as no additional materials whatsoever have to be used (the intermediate carrier is used as standard for aluminum laminates (to save on aluminum, to resist creasing and crushing, to afford better tensile strength)).

The electrode according to the invention is therefore characterised in that the gel also laterally surrounds at least in a region-wise manner the outer edges of the conductor layer and extends there to the intermediate carrier.

BRIEF DESCRIPTION OF THE DRAWING

Further advantages and details of the invention are described in greater detail with reference to the specific description hereinafter.

DETAILED DESCRIPTION OF THE INVENTION

Figure 1:
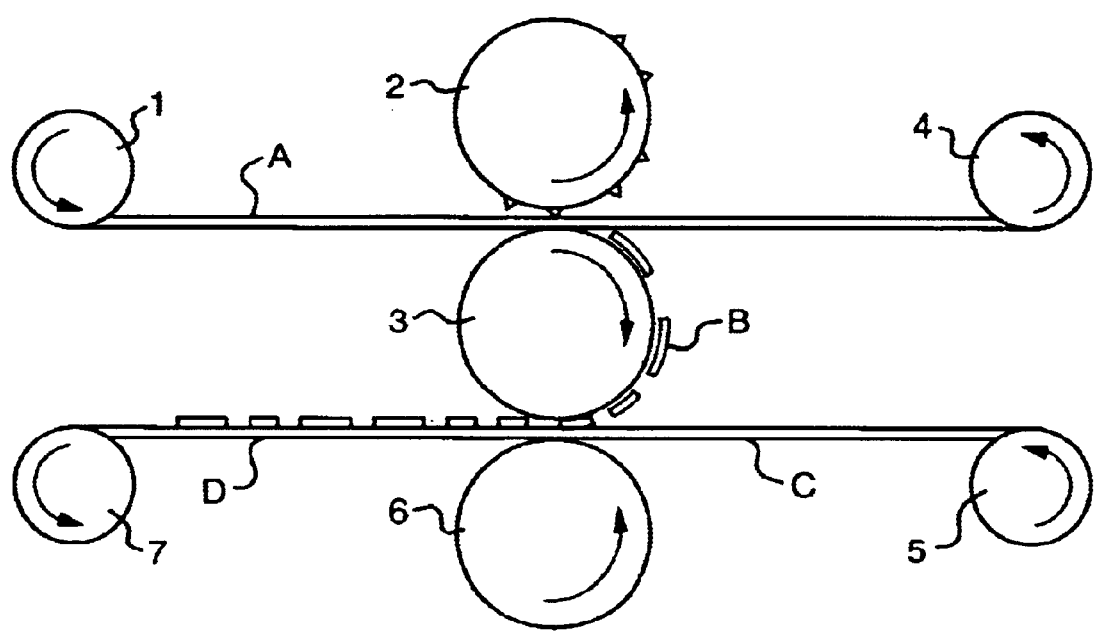
FIG. 1 shows an apparatus for producing a laminate in web form for carrying out an embodiment of the process according to the invention.

Referring to FIG. 1, a conductor layer A in web form, for example a highly conductive foil of aluminum of a thickness of 25 micrometers is unrolled from a roll 1 and conveyed through a rotary stamping machine 2. The rotary stamping machine 2 produces stampings which in respect of their final form already correspond to the form of the electrically conductive layer in the subsequently manufactured finished electrode. It will be appreciated however that it is possible for those stampings B to be connected together by thin bar portions, for reasons relating to production procedure. The stampings B are further conveyed by a counter-pressure roller 3 and the stamping waste lattice from which the stampings have been stamped and which is no longer to be put to use is wound onto the roll 4.

A non-conductive intermediate carrier C in web form, in the form of a PET foil of a thickness of 40 micrometers, is unrolled from the roll 5 and conveyed to a laminating roller 6. Between the laminating roller 6 and the counter-pressure roller 5, the highly conductive stampings B are connected to the non-conducting intermediate carrier C. That can be effected for example by a procedure whereby the conductive aluminum foil B is coated at its side towards the non-conductive PET-foil C with a thermally activatable adhesive which is activated by means of a heating device disposed in the laminating roller 6. The web laminate D with the non-conductive intermediate carrier C and the electrically conductive fields or areas B of the conductor layer, which are laminated onto the intermediate carrier C, are further conveyed for further processing, for example being rolled onto the roll 7.

An essential aspect of the invention is the fact that the conductor layer is not laminated in the form of a continuous web onto the non-conductive intermediate carrier C in web form, but is laminated thereon only in "individual fields", wherein those individual fields preferably already correspond to the final form of the conductor layer in the finished electrodes.

Figure 2A:
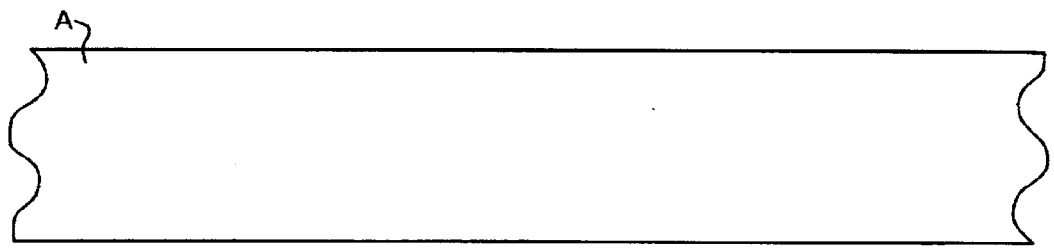
FIGS. 2a, 2b, 2c and 2d show production of the laminate according to the invention, on the basis of the components used.
Figure 2B:
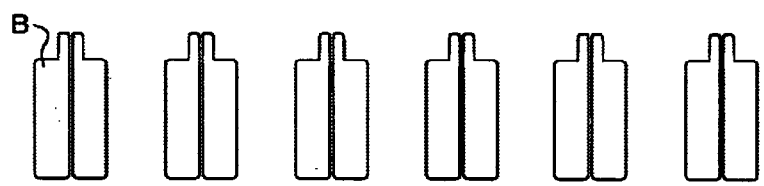
Figure 2C:
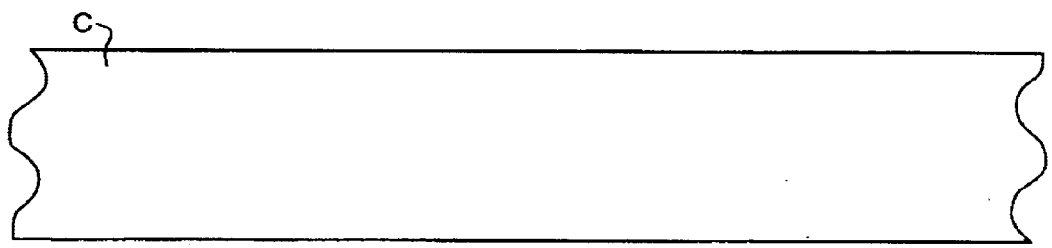
Figure 2D:
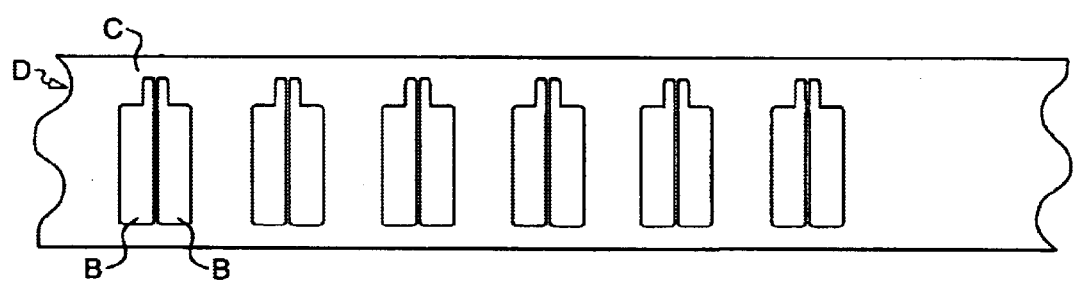

FIG. 2a shows the conductor layer (for example an aluminum foil A) while still in the form of a web. Stampings or generally fields are produced from that conductor layer by contour shaping, for example by a stamping operation. The stampings or fields are then applied to the non-conductive intermediate carrier web C shown in FIG. 2c. Finally, the result obtained in this first working step as shown in FIG. 2d is a laminate D with a non-conductive intermediate carrier C in web form and conductive fields B applied thereto.

Figure 3:
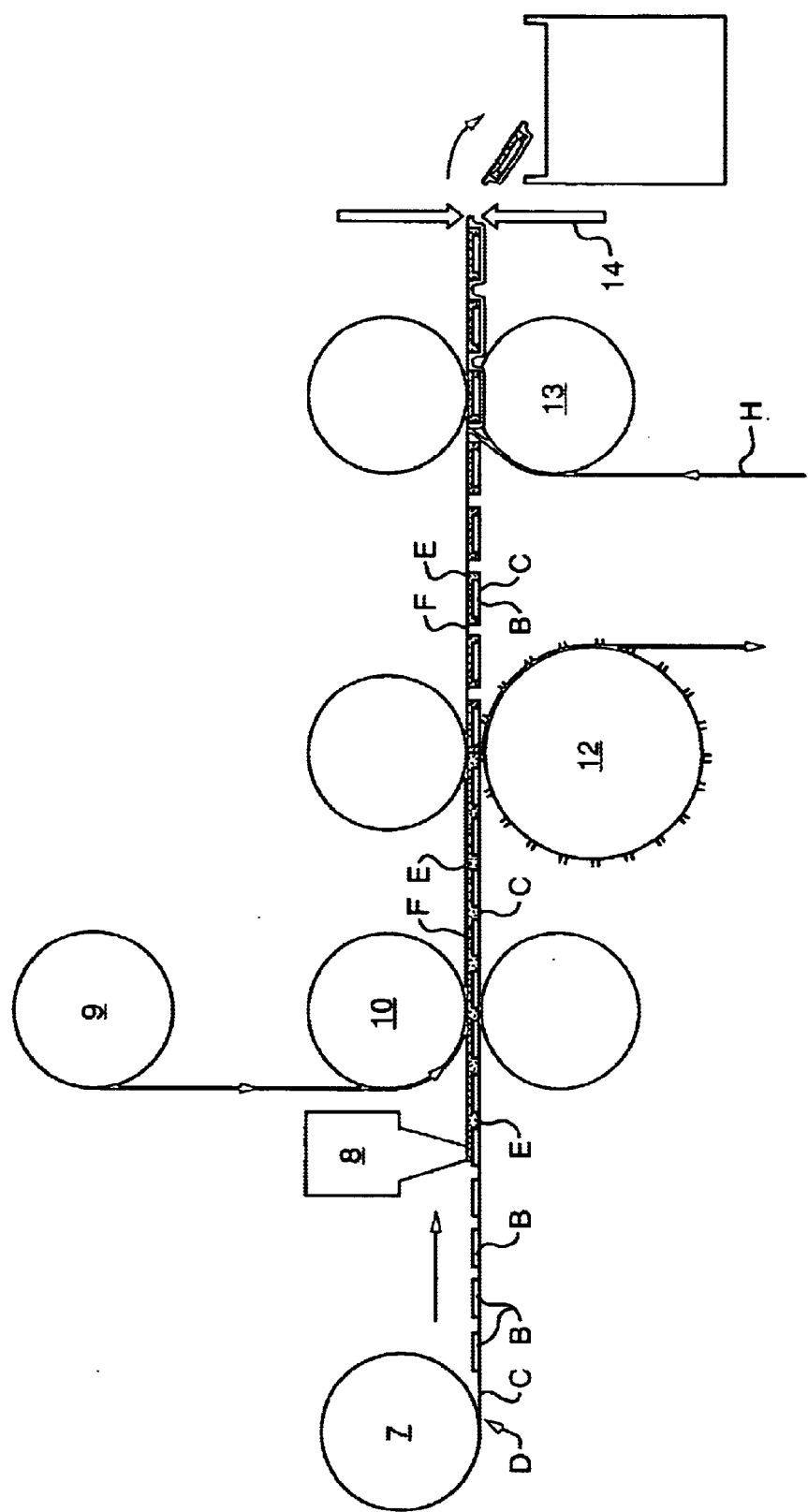
FIG. 3 shows an embodiment of an apparatus for producing medical electrodes, to which a laminate in web form which has been produced for example as in FIG. 1 is fed.
Figure 3A:
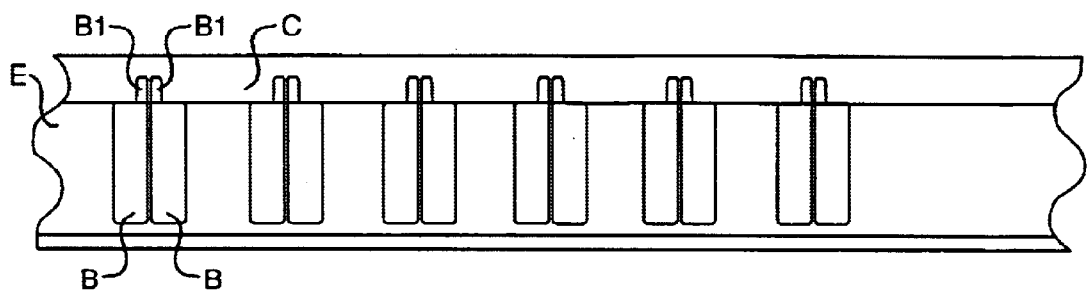
FIGS. 3a, 3b and 3c show various production stages in the production of electrodes according to the invention.

That web laminate is now subjected to further processing in order to produce the medical electrodes. That can be effected for example in a device as is shown in FIG. 3. The laminate is unrolled from a roll 7. It has the non-conductive intermediate carrier C in web form, with the electrically conductive fields B disposed thereon. In the station 8, that laminate is continuously coated with an adhesive conductive gel E, in which case the later connecting flaps or tags B1 can remain free, as shown in FIG. 3a. Then, a covering layer F of adhesive material (for example a siliconized plastic foil) comes from a supply roll by way of a contact pressure roll 10 onto the gel layer.

Figure 3B:
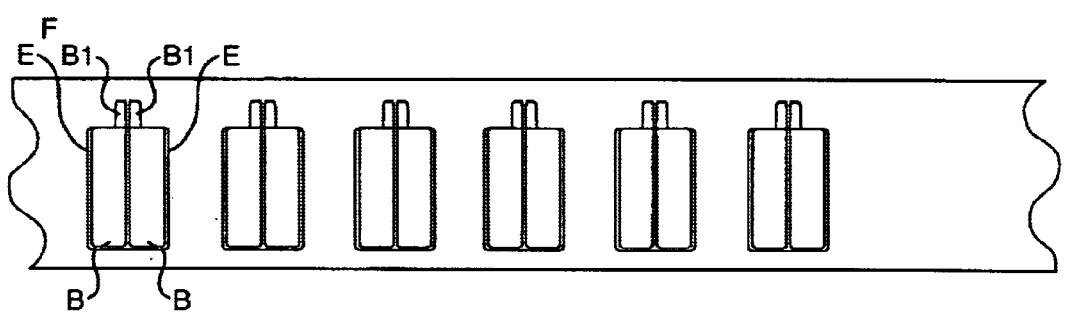
Figure 3C:
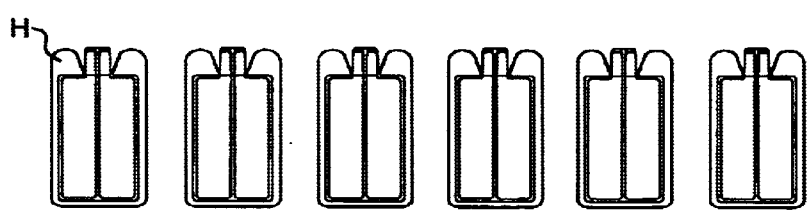

Now, in the rotary stamping machine 12, the intermediate carrier and the gel layer E but not the cover layer F are stamped therethrough, more specifically in such a way that the gel E projects laterally at least in a region-wise manner (except for the connecting flaps B1) with respect to the outer edges of the conductor layer fields B which are pre-formed in the laminate D. That then gives the situation shown in FIG. 3b. What is important is that the outer edges or boundaries of the conductor layer fields B which later come into contact with the skin by way of the gel E are reliably covered and thus cannot come directly into contact with the skin. Now, in station 13, a carrier layer of material which is adhesive on one side is laminated onto the web shown in FIG. 3b and then in the separating station (cutting or stamping) the individual finished electrodes are produced, as are diagrammatically shown in FIG. 3c. It is also mentioned that the conductor layer fields shown in FIG. 3 are shown as being continuous for the sake of simplicity, while in FIGS. 3a through 3c they are respectively of a double configuration, per electrode.

Figure 4:
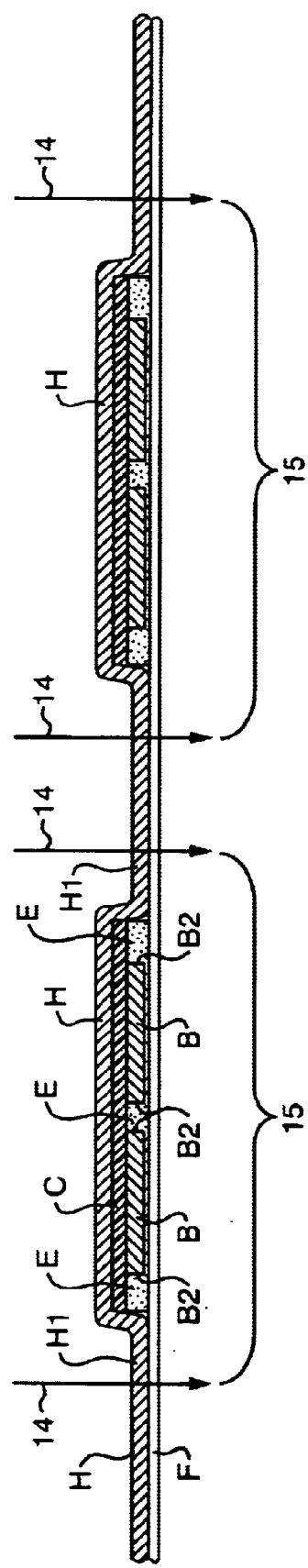
FIG. 4 shows electrodes according to the invention in a cross-section shortly before the last cutting or stamping step for separating of the individual electrodes.

The more precise structure of such a medical electrode is shown in FIG. 4. Each electrode 15 is produced by way of a separating operation 14, for example cutting or stamping, from the web used in the automated operating procedure. In this respect the layer structure is as follows: disposed on the side which faces away from the skin is a carrier material H of foam, which is adhesive on the underside. That foam material has laterally projecting flaps H1 which can be glued directly on the skin of the patient. Under that material is a laminate comprising an intermediate carrier C and electrically conductive fields B. Those conductive layers B are laterally covered with respect to the skin of the patient by an electrically conductive adhesive gel E, the gel E extending as far as the intermediate carrier C.

The thicknesses of the layers are shown as being substantially thicker in the drawings than is the case in practice, for reasons of clarity of the drawings. In actual fact it is appropriate for the thickness of the conductor layer B to be of the order of magnitude of between 20 and 15 micrometers and for the thickness of the intermediate carrier to be in the range of between 20 and 60 micrometers. In addition, the adhesive layers on the side of the carrier H, which is towards the skin, and between the conductive fields B and the intermediate carrier C, are not shown in the drawings in the form of separate layers.

In summary it can be noted that the embodiment of the process according to the invention includes a total of three stamping steps, more specifically a first stamping step in production of the laminate web as shown in FIG. 1 for region-wise application of the conductor layer to the intermediate carrier. A second stamping step involves stamping the conductive gel together with the intermediate carrier at a certain spacing around the pre-formed conductor layer fields. Then, in a third stamping step, the foam which functions as the carrier, together with the siliconized cover layer, is stamped through, in order to form the individual electrodes.

What is claimed is:

1. A process for producing medical electrodes comprising:
    applying a conductor layer to an intermediate carrier in web form to form a laminate in web form, wherein the conductor layer is applied in the form of fields which do not cover the entire intermediate carrier;
    coating the laminate on a side of the conductor layer with an electrically conductive adhesive gel to form a laminate-gel combination;
    shaping the laminate-gel combination to contour in such a way that the gel laterally projects at least in a region-wise manner with respect to the outer edges of the conductor layer fields which are pre-formed in the laminate; and affixing a carrier to the laminate-gel combination on the side remote from the gel.

2. The process of claim 1 wherein the medical electrodes produced are neutral electrodes.

3. The process of claim 1 wherein the shaping step is achieved by stamping.

4. The process of claim 1 wherein the gel laterally projects at all sides with respect to the outer edges of the conductor layer fields.

5. The process of claim 1 wherein the conductor layer fields are applied to the intermediate carrier in web form using a heat-activated adhesive.

6. The process of claim 1 wherein the conductor layer fields are formed by stamping them out of a conductor layer web.

7. The process of claim 6 wherein a rotary stamping apparatus for stamping out the conductor layer fields cooperates with a counter-pressure roller which feeds the conductor layer fields in the form of stampings to a laminating roller for lamination onto the intermediate carrier in web form.

8. The process of claim 1 wherein the form of the conductor layer fields in the laminate corresponds to the final form of the conductor layer in the finished electrodes.

9. The process of claim 1 wherein the laminate is coated on the side of the conductor layer fields with a continuous web of an electrically conductive adhesive gel.

10. The process of claim 1 further comprising covering the gel with a cover layer in web form.

11. The process of claim 10 wherein the shaping step is performed by stamping out the contour of the laminate-gel combination on the cover layer, wherein the intermediate carrier of the laminate and the gel, but not the cover layer, are stamped through and remain as stampings on the cover layer.

12. The process of claim 1 wherein the carrier is in the form of a carrier web that is adhesive on one side.

13. The process of claim 10 wherein the carrier is in the form of a carrier web that is adhesive on one side.

14. The process of claim 13 further comprising joining the carrier web to the cover layer to form the finished electrodes.

15. The process of claim 14 further comprising separating the finished electrodes.

16. The process of claim 15 wherein the separating step is achieved by stamping.

17. The process of claim 15 wherein the separating step is achieved by cutting.

* * * * *